United States Patent
Meyer et al.

(10) Patent No.: US 11,545,237 B2
(45) Date of Patent: Jan. 3, 2023

(54) MORPHOMETRIC GENOTYPING OF CELLS IN LIQUID BIOPSY USING OPTICAL TOMOGRAPHY

(71) Applicant: VISIONGATE, INC., Phoenix, AZ (US)

(72) Inventors: Michael G. Meyer, Phoenix, AZ (US); Daniel J. Sussman, Auburn, CA (US); Rahul Katdare, Bothell, WA (US); Laimonas Kelbauskas, Chandler, AZ (US); Alan C. Nelson, Gig Harbor, WA (US); Randall Mastrangelo, Gaithersburg, MD (US)

(73) Assignee: VISIONGATE, INC., Woodinville, WA (US)

( * ) Notice: Subject to any disclaimer, the term of this patent is extended or adjusted under 35 U.S.C. 154(b) by 0 days.

(21) Appl. No.: 16/650,304

(22) PCT Filed: Sep. 26, 2018

(86) PCT No.: PCT/US2018/052880
§ 371 (c)(1),
(2) Date: Mar. 24, 2020

(87) PCT Pub. No.: WO2019/067557
PCT Pub. Date: Apr. 4, 2019

(65) Prior Publication Data
US 2021/0210169 A1 Jul. 8, 2021

Related U.S. Application Data

(60) Provisional application No. 62/563,542, filed on Sep. 26, 2017.

(51) Int. Cl.
*G06T 7/00* (2017.01)
*G16B 40/20* (2019.01)
(Continued)

(52) U.S. Cl.
CPC .......... *G16B 40/20* (2019.02); *G01N 15/147* (2013.01); *G01N 15/1429* (2013.01);
(Continued)

(58) Field of Classification Search
CPC .. G16B 40/20; G01N 15/1429; G01N 15/147; G01N 15/1475; G01N 2015/1006;
(Continued)

(56) References Cited

U.S. PATENT DOCUMENTS 6,522,775 B2   2/2003   Nelson
7,738,945 B2   6/2010   Fauver et al.
(Continued)

FOREIGN PATENT DOCUMENTS

WO   2018/160998 A1   9/2018

OTHER PUBLICATIONS

Meyer et al., "The Cell-CT 3D Cell Imaging Technology Platform Enables the Detection of Lung Cancer Using the Non-Invasive LuCED Sputum Test", Jul. 6, 2015. (Year: 2015).*
(Continued)

*Primary Examiner* — Phuoc Tran
(74) *Attorney, Agent, or Firm* — Seed Intellectual Property Law Group LLP

(57) ABSTRACT

A classification training method for training classifiers adapted to identify specific mutations associated with different cancer including identifying driver mutations. First cells from mutation cell lines derived from conditions having the number of driver mutations are acquired and 3D image feature data from the number of first cells is identified. 3D cell imaging data from the number of first cells and from other malignant cells is generated, where cell imaging data includes a number of first individual cell images. A second set of 3D cell imaging data is generated from a set of normal cells where the number of driver mutations are
(Continued)

expected to occur, where the second set of cell imaging data includes second individual cell images. Supervised learning is conducted based on cell line status as ground truth to generate a classifier.

28 Claims, 7 Drawing Sheets

(51) Int. Cl.
```
   G06T 7/194      (2017.01)
   G06T 7/11       (2017.01)
   G01N 15/14      (2006.01)
   G06K 9/62       (2022.01)
   G06V 10/40      (2022.01)
   G06V 20/64      (2022.01)
   G06V 20/69      (2022.01)
   G01N 15/10      (2006.01)
```
(52) U.S. Cl.
CPC ....... *G01N 15/1475* (2013.01); *G06K 9/6256* (2013.01); *G06T 7/0012* (2013.01); *G06T 7/11* (2017.01); *G06T 7/194* (2017.01); *G06V 10/40* (2022.01); *G06V 20/64* (2022.01); *G06V 20/695* (2022.01); *G06V 20/698* (2022.01); *G01N 2015/1006* (2013.01); *G01N 2015/1445* (2013.01); *G06T 2207/10101* (2013.01); *G06T 2207/20081* (2013.01); *G06T 2207/30024* (2013.01); *G06V 2201/03* (2022.01)

(58) Field of Classification Search
CPC ....... G01N 2015/1445; G01N 15/1434; G01N 21/4795; G06K 9/6256; G06T 7/0012; G06T 7/11; G06T 7/194; G06T 2207/10101; G06T 2207/20081; G06T 2207/30024; G06V 10/40; G06V 20/64; G06V 20/695; G06V 20/698; G06V 2201/03; A61B 5/006
See application file for complete search history.

(56) References Cited

U.S. PATENT DOCUMENTS

| | | | |
|---|---|---|---|
| 7,835,561 B2 | 11/2010 | Meyer et al. | |
| 7,907,765 B2 | 3/2011 | Fauver et al. | |
| 8,254,023 B2 | 8/2012 | Watson et al. | |
| 9,594,072 B2 | 3/2017 | Meyer et al. | |
| 10,733,726 B2* | 8/2020 | Lloyd | G06K 9/6267 |
| 2003/0031352 A1* | 2/2003 | Nelson | G01N 33/574 |
| | | | 382/131 |
| 2017/0003267 A1 | 1/2017 | Meyer et al. | |

OTHER PUBLICATIONS

Bougen-Zhukov et al., "Large-Scale Image-Based Screening and Profiling of Cellular Phenotypes," *Cytometry Part A* 91A:115-125, 2017.

Bray et al., "Workflow and Metrics for Image Quality Control in Large-Scale High-Content Screens," *Journal of Biomolecular Screening* 17(2):266-274, 2012.

Breiman, "Random Forests," *Machine Learning* 45:5-32, 2001.

Deans, "*The Randon Transform and Some of Its Applications,*" Dover Publications, Inc., Mineola, New York, 2007, 308 pages.

Fauver et al., "Three-dimensional imaging of single isolated cell nuclei using optical projection tomography," *Optics Express* 13(11):4210-4223, 2005.

Fuchs et al., "Clustering phenotype populations by genome-wide RNAi and multiparametric imaging," *Molecular Systems Biology* 6:310, 2010. (13 pages).

Meyer et al., "The Cell-CT 3-Dimensional Cell Imaging Technology Platform Enables the Detection of Lung Cancer Using the Noninvasive LuCED Sputum Test," *Cancer Cytopathology* 123:512-523, 2015.

Mukherji et al., "Genome-wide functional analysis of human cell-cycle regulators," *PNAS* 103(40):14819-14824, 2006.

Nicolazzo et al., "Monitoring PD-L1 positive circulating tumor cells in non-small cell lung cancer patients treated with the PD-1 inhibitor Nivolumab," *Scientific Reports* 6:31726, 2016. (8 pages).

Nishino et al., "Histological and cytomorphologic features of ALK-rearranged lung adenocarcinomas," *Modern Pathology* 25:1462-1472, 2012.

Patel et al., "PD-L1 Expression as a Predictive Biomarker in Cancer Immunotherapy," *Molecular Cancer Therapeutics* 14(4):847-856, 2015.

Rohban et al., "Systematic morphological profiling of human gene and allele function via Cell Painting," *eLife* 6: e24060, 2017. (23 pages).

Rossi et al., "Morphological Parameters Able to Predict BRAF$^{V600E}$-Mutated Malignancies on Thyroid Fine-Needle Aspiration Cytology: Our Institutional Experience," *Cancer Cytopathology* 122:883-891, 2014.

Singh et al., "A Gene Expression Signature Associated with "K-Ras Addiction" Reveals Regulators of EMT and Tumor Cell Survival," *Cancer Cell* 15:489-500, 2009.

Suda et al., "EGFR T790M Mutation—A Double Role in Lung Cancer Cell Survival?," *Journal of Thoracic Oncology* 4(1): Jan. 4, 2009.

Vécsey-Semjén et al., "Novel colon cancer cell lines leading to better understanding of the diversity of respective primary cancers," *Oncogene* 21:4646-4662, 2002.

Wilbur et al., "Automated 3-Dimensional Morphologic Analysis of Sputum Specimens for Lung Cancer Detection: Performance Characteristics Support Use in Lung Cancer Screening," *Cancer Cytopathology* 123:548-556, 2015.

Xu et al., "Up-regulation of the Hippo pathway effector TAZ renders lung adenocarcinoma cells harboring EGFR-T790M mutation resistant to gefitinib," *Cell & Bioscience* 5(1): 2015. (9 pages).

Finkelstein et al., "Papillary thyroid carcinomas with and without BRAF V600E mutations are morphologically distinct," *Histopathology* 60:1052-1059, 2012.

Hansen et al., "PD-L1 Testing in Cancer—Challenges in Companion Diagnostic Development," *JAMA Oncoloyy* 2(1):15-16, 2016.

* cited by examiner

MORPHOMETRIC GENOTYPING OF CELLS IN LIQUID BIOPSY USING OPTICAL TOMOGRAPHY

TECHNICAL FIELD

The present invention relates to optical tomography on a cellular and sub-cellular scale. More particularly, the invention relates to a method and apparatus for morphometric genotyping of cells in fluid flow in a capillary tube using optical tomography.

BACKGROUND

With personalized medicine on the increase due to the advent of cancer therapies that target specific tumor genotypes or driver mutations, the development of rapid diagnostic tools is paramount. An example of tumor genotype that impacts therapy is the status of PD-L1 expression, which in multiple cancers, including melanoma, lung, kidney, and bladder cancers determines if it will respond to immune checkpoint inhibition anticancer therapy (Patel and Kurzrock[14], Hansen and Siu[8]). Examples of therapies that target driver mutations for lung cancer are erlotinib, gefitinib, afatinib, dacomitinib or osimertinib for primary EGFR mutations; osimertinib (TAGRISSO, AstraZeneca Pharmaceuticals, LP) for the EFGR T790M mutation; crizotinib, ceritinib, alectinib or larolatinib for ALK rearrangements as primary treatment and secondary resistance mutations or rearrangements treatments; larotrectinib, entrectinib and TPX-0005 (TP Therapeutics) for TRK fusion kinase activating alterations; crizonitib for MET Exon 14 alterations; RXDX-105 (Ignyta/Genentech/Roche) and Loxo-292 (Loxo Oncology) for RET alterations; dabrafenib and trametinib alone or in combination for BRAF V600E/MEK alterations; and crizotinib or cabozantinib for ROS1 translocation. While molecular tools such as allele specific PCR, genomic sequencing, and fluorescence in situ hybridization (FISH) are able to detect specific mutations, these assays require either invasive procedures such as tumor biopsy or lengthy protocols that require single cell capture of circulating tumor cells. A more rapid approach, as described below using the VisionGate Cell-CT™ platform, is to identify specific mutations based on their conferring morphometric changes to structure of the cellular and/or nuclear architecture biomarkers which can be quantified optically.

Bougen-Zhukov et al.[1] present a review of large scale 2-D image-based screening and profiling of cellular phenotypes. 2-D image screening platforms utilizing various morphology based quantitative features have been developed and used as a means to characterize gene associations and the activity of bioactive compounds. As examples: 1) Mukherji et al.[10] analyzing images acquired by quantitative fluorescence microscopy screened>95% of the protein-coding genes using siRNA to inhibit gene expression. They found 1,152 targeted genes that strongly affected cell cycle progression and were able to cluster them into eight distinct phenotypic categories based on phase of arrest, nuclear area, and nuclear morphology. 2) Likewise, Fuchs et al.[7] used quantitative descriptors derived from high-throughput imaging to generate multiparametric phenotypic profiles for screening 800 gene targets using RNAi to inhibit expression. They found that the profiles predicted functions of genes by phenotypic similarity. 3) A "cell painting" assay was developed that uses fluorescent probes to highlight nuclei, nucleoli, cytoskeleton, golgi, endoplasmic reticulum, and mitochondria. Combined with high-throughput image analysis the assay detects a range of cellular phenotypes and has been used to classify bioactive compounds, as well as cDNA construct expression (Bray et al.[2]; Bougen-Zhukov et al.[1]; and Rohban et al.[16]).

A number of studies have demonstrated that mutation status and changes in gene expression in tumor cells lead to changes in cellular morphology. The following examples support this contention: 1) Papillary thyroid carcinomas with a BRAF mutation are morphologically distinct from those that do not contain a BRAF mutation (Finkelstein et al.[16]). Based on fine needle aspiration cytology Rossi et al.[17] found that focal plump cells harboring a distinctive sickle nuclear shape were found only in the mutated cases and demonstrated 100% cytohistological concordance. 2) Nicolazzo et al.[13] reported that in NSCLC patients the vast majority of PD-L1(+) circulating tumor cells (CTCs) presented an irregular shape, mostly elongated and with a peripheral nucleus, as compared to the more frequent round shape observed in PD-L1(−) CTCs. 3) VeÂcsey-SemjeÂn et al.[21] examined eight low passage number human colon cancer cell lines and found cell morphology and biomarker expression to be highly variable. 4) Singh et al.[19] found a gene expression signature and morphological changes associated with "K-Ras addiction". NSCLC lines that were K-Ras-dependent exhibited classic epithelial morphology while the K-Ras-lndependent cells were poorly differentiated. Mutations that lead to these phenotypes have implications with respect to personalized treatment. 5) Nishino et al.[12] reported that ALK-rearranged lung adenocarcinomas had distinct morphological differences when compared to adenocarcinomas with wild type ALK. They developed a morphology-based scoring system for predicting ALK rearrangement that had a sensitivity of 88% and a specificity of 45%.

With respect to the EGFR T790M mutation that confers resistance to gefitinib, afatinib, dacomitinib and erlotinib, while no mutation-specific morphological changes have been reported, the mutation confers a growth advantage (Suda et al.[20]) and also leads to increased expression of TAZ (Xu et al.[23]), both of which might confer morphological changes.

As described above, morphological changes based on driver mutations have been observed in multiple types of cancers. While the data presented below establishes the ability of the Cell-CT™ platform to perform morphometric genotyping on lung adenocarcinoma cell lines, the utility of this technology extends to other cancers and other disorders.

Advances in 3D imaging of biological cells using optical tomography have been implemented by Nelson as disclosed, for example, in U.S. Pat. No. 6,522,775, issued Feb. 18, 2003, and entitled "Apparatus and Method for Imaging Small Objects in a Flow Stream Using Optical Tomography," the full disclosure of which is incorporated by reference. Further major developments in the field are taught in Fauver et al., U.S. Pat. No. 7,738,945, issued Jun. 15, 2010, entitled "Method and Apparatus for Pseudo-Projection Formation for Optical Tomography," (Fauver '945) and Fauver et al., U.S. Pat. No. 7,907,765, issued Mar. 15, 2011, entitled "Focal Plane Tracking for Optical Microtomography," (Fauver '765) the full disclosures of Fauver '945 and Fauver '765 are also incorporated by reference. Building on the teachings therein, an early lung cancer detection technology has been developed by VisionGate, Inc., Phoenix, Ariz. to provide measurement advantages that have demonstrated a great improvement in the operating characteristics of conventional morphologic cytology analyses.

The Cell-CT™ platform made by VisionGate, Inc. of Phoenix, Ariz. is an automated, high-resolution 3D tomographic microscope and computing system for imaging cells in flow. The Cell-CT™ platform computes 3D cell images with equal spatial resolution in all dimensions (isotropic resolution) allowing measurements to be independent of orientation, as opposed to conventional optical imaging methods. Further, eliminating the focal plane ambiguity and view orientation dependencies typical of conventional microscopy provides information content to automatically recognize a broad spectrum of cell types, and unambiguously identify rare abnormal cells in a predominantly normal cell population Processing in such an optical tomography system begins with specimen collection and preparation. For diagnostic applications in lung disease, patient sputum can be collected non-invasively in a clinic or at home. At the clinical lab, the sputum is processed to remove non-diagnostic material, fixed and then stained. Stained specimens are then mixed with an optical gel, and the suspension is injected into a microcapillary tube. Images of objects, such as cells, in the specimen are collected while the cells are rotated around 360-degrees relative to the image collection optics in an optical tomography system. The resultant images comprise a set of extended depth of field images from differing perspectives called "pseudo-projection images." The set of pseudo-projection images can be mathematically reconstructed using backprojection and filtering techniques to yield a 3D reconstruction of a cell of interest. Having isometric or roughly equal resolution in all three dimensions is an advantage in 3D tomographic cell imaging, especially for quantitative feature measurements and image analysis.

The 3D reconstructed digital image then remains available for analysis in order to enable the quantification through the measurement of sub-cellular structures, molecules or molecular probes of interest. An object such as a biological cell may be stained or labeled with at least one absorbing contrast agent or tagged molecular probe, and the measured amount and structure of this biomarker may yield important information about the disease state of the cell, including, but not limited to, various cancers such as lung, breast, prostate, cervical, stomach and pancreatic cancers, and various stages of dysplasia.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

The instant invention overcomes the deficiencies found in the art by providing, for the first time, a method to develop one or more morphometric classifiers to identify the specific mutation(s) that drive the cancer process. The method is adaptable to the specific objectives that one may have. Results presented show that a specific driver mutation may be detected in a highly accurate way. This invention, therefore, has strong significance for the evolving practice of targeting cancer therapy to the specific genetic profile that presents in a tumor, allowing more efficient cancer management with far fewer side effects.

In one aspect, a classification training method for training classifiers adapted to identify specific mutations associated with different cancer including identifying a number of driver mutations is described. A number of first cells from a number of mutation cell lines derived from conditions having the number of driver mutations are acquired and 3D image feature data from the number of first cells is identified. A first set of 3D cell imaging data from the number of first cells and from a number of other malignant cells is generated, where the first set of cell imaging data includes a number of first individual cell images. A second set of 3D cell imaging data is generated from a set of normal cells where the number of driver mutations are expected to occur, where the second set of cell imaging data includes a number of second individual cell images. Supervised learning is conducted based on cell line status as ground truth. A classifier is generated from the supervised learning.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

Figure 1:
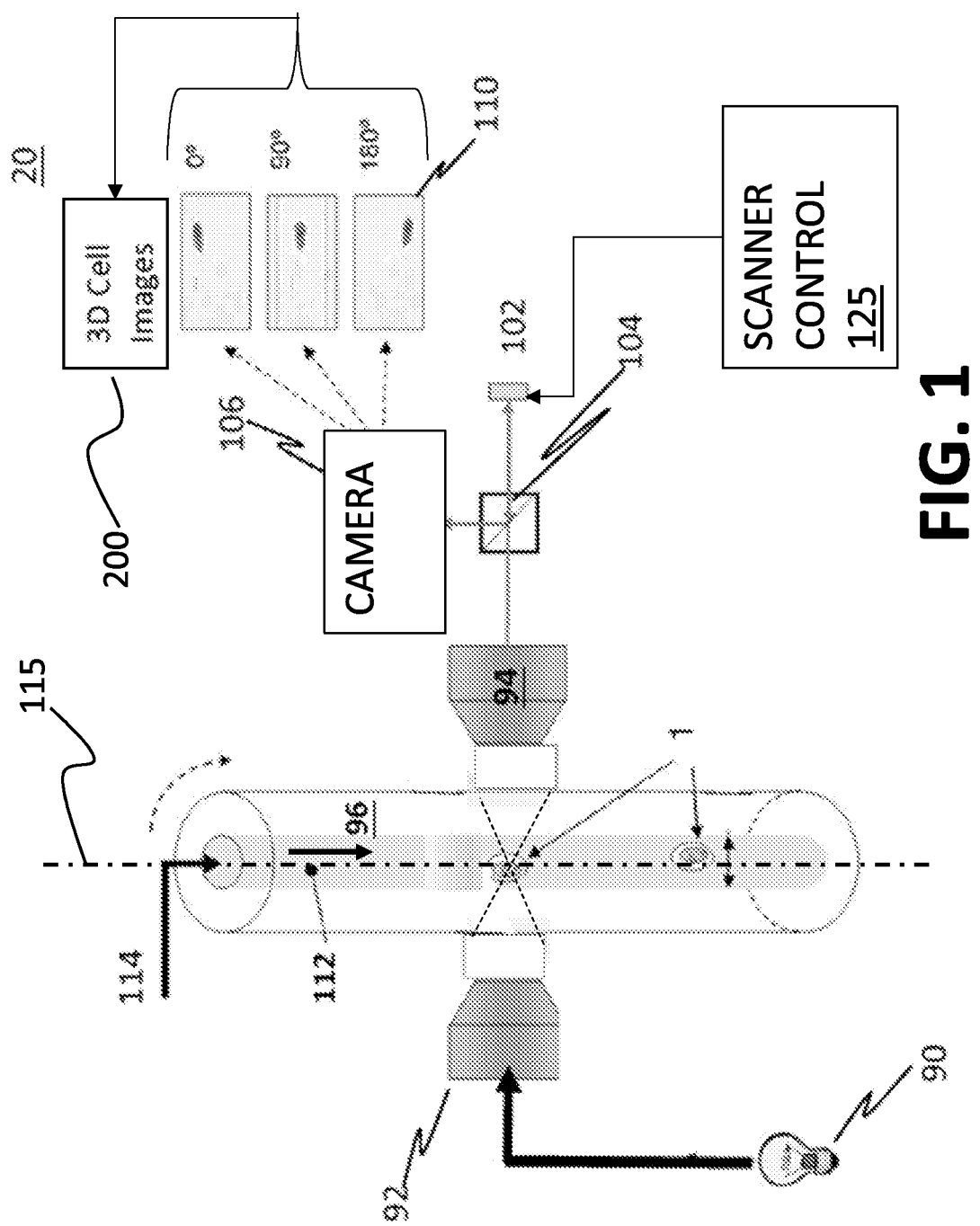
FIG. 1 schematically shows system components of a 3D optical tomography imaging system used in a lung cancer test system.

In the drawings, identical reference numbers call out similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not necessarily intended to convey any information regarding the actual shape of the particular elements, and have been solely selected for ease of recognition in the drawings.

DETAILED DESCRIPTION OF THE PREFERRED EMBODIMENTS

The following disclosure describes a method and apparatus for morphometric genotyping of cells using optical tomography. Several features of methods and apparatus in accordance with example embodiments are set forth and described with reference to the figures. It will be appreciated that methods and apparatus in accordance with other example embodiments can include additional procedures or features different than those shown in the figures. Example embodiments are described herein with respect to morphometric genotyping of cells in fluid flow in a capillary tube in an optical tomography cell imaging system. However, it will be understood that these examples are for the purpose of illustrating the principles, and that the invention is not so limited.

Definitions

Generally, as used herein, the following terms have the following meanings, unless the use in context dictates otherwise:

The use of the word "a" or "an" when used in conjunction with the term "comprising" in the claims or the specification means one or more than one, unless the context dictates otherwise. The term "about" means the stated value plus or minus the margin of error of measurement or plus or minus 10% if no method of measurement is indicated. The use of the term "or" in the claims is used to mean "and/or" unless explicitly indicated to refer to alternatives only or if the alternatives are mutually exclusive. The terms "comprise", "have", "include" and "contain" (and their variants) are open-ended linking verbs and allow the addition of other elements when used in a claim.

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one example" or "in an embodiment" in various places throughout this specification are not necessarily all referring to the same embodiment or example. Furthermore, the particular features, structures, or characteristics may be combined in any suitable manner in one or more embodiments.

"Adequacy" refers to the content of the specimen and defines a limit for target cells to determine if a sufficient cellular pellet has been analyzed.

"Capillary tube" has its generally accepted meaning and is intended to include transparent microcapillary tubes and equivalent items with an inside diameter generally of 500 microns or less, but larger diameters could be used.

"Capillary radius" means the radius of an object as referenced to the axial center locus of a capillary tube.

"Cell" means biological cell such as a human, mammal or animal cell.

"Cell-CT™ platform" refers to an optical tomography system manufactured by VisionGate, Inc. of Phoenix, Ariz. incorporating teachings of the Nelson and Fauver patents referenced herein above and improvements of those teachings.

"Depth of field" is the length along the optical axis within which the focal plane may be shifted before an unacceptable image blur for a specified feature is produced.

"Enrichment" refers to the process of extracting target cells from a raw specimen. The process yields an enriched pellet whose cells can then be more efficiently imaged on the Cell-CT™ platform.

"Frame rate" refers to the number of images captured per second by a camera or image sensors and is typically measured in frames per second (fps).

"LuCED® test" refers to an early lung cancer detection test employing the Cell-CT™ platform as developed by VisionGate, Inc. of Phoenix, Ariz. incorporating the teachings of the Nelson and Fauver patents referenced hereinabove and improvements of those teachings.

"The LuCED® process" refers to the mechanism of 3D cell reconstruction, classification to find abnormal cells, and pathology confirmation.

"Optical axis" refers to a line passing through the center of curvature of the lens or spherical mirror in parallel to the axis of symmetry. As used herein, optical axis substantially coincides with the "focus axis" of a microscope objective lens.

"Pseudo-projection" includes a single image representing a sampled volume of extent larger than the native depth of field of the optics where a pseudo-projection image thus formed includes an integration of a range of focal plane images from a fixed viewpoint. The concept of a pseudo-projection is taught in Fauver '945.

"Processor" and "computer processor" as used in this specification encompass a personal computer, a tablet computer, a smart phone, a microcontroller, a microprocessor, a field programmable object array (FPOA), a digital signal processor (DSP), an application-specific integrated circuit (ASIC), a field programmable gate array (FPGA), a programmable logic array (PLA), or any other digital processing engine, device or equivalent capable of executing software code and equivalents.

"Program" or "computer program" refers to software code or hardwired code including a series of process steps capable of being executed by a processor as in a computer software algorithm.

"Sample" means a finished cellular preparation that is ready for analysis, including all or part of an aliquot or specimen.

"Scanning," as used herein, means translating a microscope lens along an optical axis or changing the optical path distance by some other mechanism, such as a scanning mirror, so as to move its focal plane through a space, such as a capillary tube wherein an object is flowing.

"Specimen" means a complete product obtained from a single test or procedure from an individual patient (e.g., sputum submitted for analysis, a biopsy, or a nasal swab). A specimen may be composed of one or more objects. The result of the specimen diagnosis becomes part of the case diagnosis.

"Subject" as used herein means a human patient.

"Target Cell" refers to a cell from a specimen whose characterization or enumeration is especially desired. For example, in the LuCED® test, the target cells are the bronchial epithelial cells. A minimum number of these must be enumerated during the test in order for a specimen to be considered as adequate.

"Target Object" refers to a microscopic object of interest, as for example, a biological cell, cell nucleus, organelle, a human cell, mammal cell, item, thing, other entity or other microscopic biological feature. Any object of interest may be designated as a target object including target cells.

"Threshold" as used in the context of image processing includes a decision boundary value for any measurable characteristic of a feature. Thresholds may be selected or set according to instrument specifications, acceptable error rates, statistics, or other criteria according to accepted pattern recognition principles.

"Voxel" is used in the context of image processing is a volume element on a 3D grid.

EXAMPLES

As described hereinbelow, in one aspect, a classification training method for training classifiers adapted to identify specific mutations associated with cancer comprises:

identifying a plurality of driver mutations;

acquiring a plurality of first cells from a plurality of mutation cell lines derived from conditions having the plurality of driver mutations;

identifying 3D image feature data from the plurality of first cells;

generating a first set of 3D cell imaging data from the plurality of first cells and from a plurality of other malignant cells, where the first set of cell imaging data includes a plurality of first individual cell images;

generating a second set of 3D cell imaging data from a set of normal cells where the plurality of driver mutations is expected to occur, where the second set of cell imaging data includes a plurality of second individual cell images;

operating supervised learning based on cell line status as ground truth; and generating a classifier from the supervised learning.

In another aspect, the act of identifying 3D image feature data comprises processing reconstructed 3D cell images to define a plurality of features of cell morphology.

In another aspect, the plurality of features are selected from the group consisting of cell volume, nuclear volume, ratio of nuclear to cytoplasm volume, shape features to define pleomorphisms in the nuclear envelope, features to characterize distribution and texture of the chromatin within the nucleus, features to count and find the size of nucleoli, features to represent the appearance of nuclear grooves and combinations thereof.

In another aspect, generating a classifier comprises:

segmenting each of the plurality of first individual cell images;

separating a nucleus from the segmented first cell image;

identifying a plurality of morphometric feature sets that correlate with each driver mutation from the plurality of driver mutations;

isolating malignant cells from normal cells by comparing morphological feature values; and separating malignant subtypes.

In another aspect, generating a classifier further comprises producing a series of binary classifiers to isolate a plurality of target cells derived from the plurality of first cells.

In another aspect, producing a series of binary classifiers comprises:

producing a first classifier trained for isolation of malignant cells from other normal cells;

producing a second classifier for separating malignant subtypes; and producing at least one subsequent classifier to isolate mutation driver cell subtypes.

In another aspect, the act of isolating malignant cells comprises isolating adenocarcinoma from other malignant cell types; and isolating a specific driver mutation within adenocarcinoma.

In another aspect, the adenocarcinoma is selected from the group consisting of Adenocarcinoma cell lines, A549 (EGFR wild-type, CDKN2A–c.1_471del471, KRAS–p.G12S), NCI-H1650 (EGFR– p.E746_A750del, CDKN2A– c.1_471del471, TP53– c.673-2A>G), NCI-H1975 (EGFR-T790M, CDKN2A– p.E69*, PIK3CA–p.G118D, TP53– p.R273H), NCI-H2228 (EML4-ALK+, CDKN2A– c.1_471del471, RB1– p.E204fs*10, TP53–p.Q331* high PD-L1) and combinations thereof.

In another aspect, the plurality of cells is selected from the group consisting of a biological cell, bronchial epithelial cells, a cell nucleus, an organelle, a human cell, mammal cell, a microscopic biological feature and combinations thereof.

In another aspect, the plurality of cells is selected from the group consisting of objects obtained from specimens including sputum, blood, urine, cervical scrapes, bowel scrapes, skin scrapes, plural effusion and a liquid biopsy.

In another aspect, a classifier is trained in accordance with the method above.

In another aspect, a method for morphometric genotyping of cells in fluid flow in a capillary tube using optical tomography comprises:

a) enriching a plurality of cells;

b) embedding the plurality of enriched cells into an optical medium;

c) injecting the plurality of embedded cells into a capillary tube;

d) applying pressure to the plurality of embedded cells until at least one of the plurality of embedded cells appears in a field of view of an optical tomography viewing subsystem;

e) operating the optical tomography system to acquire a plurality of pseudo-projection images of the at least one embedded cell that is in the field of view by rotating the capillary tube about a tube axis to generate a plurality of pseudo-projection images at different views;

f) repeating acts d) and e) to provide a set of pseudo-projection images for each embedded cell;

g) reconstructing each embedded cell using data from the set of pseudo-projection images to produce a set of 3D cell image reconstructions;

h) segmenting each 3D image of the set of 3D cell image reconstructions to separate a cell image from background;

i) further segmenting the cell image to separate a nucleus from the cell image;

k) computing a plurality of morphological features characteristic of mutation drivers from each cell image;

i) operating a biological specimen classifier to determine a feature value from the plurality of morphological features characteristic of mutation drivers; and m) classifying the 3D cell image into a cell type category by comparing the feature value to a predetermined boundary value.

In another aspect, a method for stepwise isolation of a plurality of cancer mutation drivers comprises:

providing a plurality of 3D reconstruction images to a first morphological classifier, where the 3D reconstruction images represent a plurality of cell types;

operating the first morphological classifier to isolate the plurality of cell types into normal and malignant cell types or dysplastic cell types;

next, operating a second morphological classifier on the malignant cell types to isolate SCLC: NCI-H69 type cells from other malignant cells;

next, operating a third morphological classifier on the other malignant cells to isolate Adeno: SW900 from other adenocarcinoma type cells;

next, operating a fourth morphological classifier on the other adenocarcinoma type cells to isolate Adeno: ALK+, NCI-H2228 cell types from other remaining cell types;

next, operating a fifth morphological classifier on the other remaining cell types to further isolate Adeno: Wild type, A549 from EGFR+ Adeno cell types; and next, operating a sixth morphological classifier to further isolate Adeno: T790M, NCI-H1975 from Adeno: EGFR–p.E746_A750del.

In another aspect, the 3D reconstruction images are derived from a plurality of optical tomography cell images.

In another aspect, the first through sixth classifiers are generated by acts comprising:
 segmenting each of the plurality of 3D reconstruction images;
 separating a nucleus from each segmented cell image;
 identifying a plurality of morphometric feature sets that correlate with each cancer driver mutation from the plurality of cancer driver mutations;
 isolating malignant cells from normal cells by comparing morphological feature values; and
 separating malignant subtypes.

In another aspect, generating a classifier further comprises producing a series of binary classifiers to isolate a plurality of target cells derived from the plurality of first cells.

In another aspect, producing a series of binary classifiers comprises:
 producing a first classifier trained for isolation of malignant cells from other normal cells;
 producing a second classifier for separating malignant subtypes; and
 producing at least one subsequent classifier to isolate mutation driver cell subtypes.

In another aspect, the act of isolating malignant cells comprises isolating
 adenocarcinoma from other malignant cell types; and isolating a specific driver mutation within adenocarcinoma.

In another aspect, a classification training system for training classifiers adapted to identify specific mutations associated with cancer comprises:
 means for identifying a plurality of driver mutations;
 means for acquiring a plurality of first cells from a plurality of mutation cell lines derived from conditions having the plurality of driver mutations;
 means for identifying 3D image feature data from the plurality of first cells;
 means for generating a first set of 3D cell imaging data from the plurality of first cells and from a plurality of other malignant cells, where the first set of cell imaging data includes a plurality of first individual cell images;
 means for generating a second set of 3D cell imaging data from a set of normal cells where the plurality of driver mutations is expected to occur, where the second set of cell imaging data includes a plurality of second individual cell images;
 means for operating supervised learning based on cell line status as ground truth; and
 means for generating a classifier from the supervised learning.

In another aspect, the means of identifying 3D image feature data comprises processing reconstructed 3D cell images to define a plurality of features of cell morphology.

In another aspect, the plurality of features is selected from the group consisting of cell volume, nuclear volume, ratio of nuclear to cytoplasm volume, shape features to define pleomorphisms in the nuclear envelope, features to characterize distribution and texture of the chromatin within the nucleus, features to count and find the size of nucleoli, features to represent the appearance of nuclear grooves and combinations thereof.

In another aspect, the means for generating a classifier comprises:
 a processor including a program for segmenting each of the plurality of first individual cell images;
 the processor further including a program for separating a nucleus from the segmented first cell image;
 the processor further including a program for identifying a plurality of morphometric feature sets that correlate with each driver mutation from the plurality of driver mutations;
 the processor further including a program for isolating malignant cells from normal cells by comparing morphological feature values; and
 the processor further including a program for separating malignant subtypes.

In another aspect, the means for generating a classifier further comprises the processor further including a program for producing a series of binary classifiers to isolate a plurality of target cells derived from the plurality of first cells.

In another aspect, the means for producing a series of binary classifiers comprises:
 the processor further including a program for producing a first classifier trained for isolation of malignant cells from other normal cells;
 the processor further including a program for producing a second classifier for separating malignant subtypes; and
 the processor further including a program for producing at least one subsequent classifier to isolate mutation driver cell subtypes.

In another aspect, the program for producing a first classifier trained for isolation of malignant cells from other normal cells comprises
 a program for isolating adenocarcinoma from other malignant cell types; and
 a program for isolating a specific driver mutation within adenocarcinoma.

In another aspect, the adenocarcinoma is selected from the group consisting of Adenocarcinoma cell lines, A549 (EGFR wild-type, CDKN2A–c.1_471del471, KRAS– p.G12S), NCI-H1650 (EGFR– p.E746_A750del, CDKN2A– c.1_471del471, TP53– c.673-2A>G), NCI-H1975 (EGFR-T790M, CDKN2A– p.E69*, PIK3CA– p.G118D, TP53– p.R273H), NCI-H2228 (EML4-ALK+, CDKN2A– c.1_471del471, RB1– p.E204fs*10, TP53– p.Q331* high PD-L1) and combinations thereof.

In another aspect, the plurality of cells is selected from the group consisting of a biological cell, bronchial epithelial cells, a cell nucleus, an organelle, a human cell, mammal cell, a microscopic biological feature and combinations thereof.

In another aspect, the plurality of cells is selected from the group consisting of objects obtained from specimens including sputum, blood, urine, cervical scrapes, bowel scrapes, skin scrapes, plural effusion and a liquid biopsy.

Referring to FIG. 1, system components of a 3D optical tomography imaging system used in a lung cancer test system are schematically shown. The cell imaging system 20 is an automated, high-resolution 3D tomographic microscope and computing system for imaging cells in flow. Included are an illumination source 90 optically coupled to a condenser lens 92 which optically cooperates with an objective lens 94 for scanning images of objects 1 contained in a capillary tube 96. Images are obtained by scanning the volume occupied by the object by an oscillating mirror 102 and transmitted through a beam-splitter 104 to a high-speed camera 106. The high-speed camera produces a plurality of pseudo-projection images 110. A set of pseudo-projection images for numerous axial tube rotation positions is produced for each object. In one example using the VisionGate Cell-CT™ platform, imaging is performed on a small-volume liquid suspension of cells. Because the Cell-CT™ platform is adept at separating closely coincident objects, a narrowly focused core of single file cell flow (a requirement in standard flow cytometry) is unnecessary.

For lung cancer detection, for example, these cells are obtained from an enriched epithelial cell population. The operation of examples of lung cancer test systems are described in the Nelson and Fauver references incorporated by reference hereinabove as well as other patents including U.S. Pat. No. 8,254,023 to Watson et al., issued Aug. 28, 2012 and entitled, "Optical Tomography System with High-Speed Scanner," which is also incorporated herein by reference. In operation, stained biological cell 1 is suspended in optical media 112 and injected into a capillary tube 96 having, for example, a 60 µm inner diameter. The optical media 112 is typically a fluid filled cylindrical space centered around a central axis 115 running through the capillary tube 96.

Because the cells are suspended in a fluid medium, they are prone to a small amount of movement while pseudo-projection images 110 are collected. Cell images in the pseudo-projections, therefore, must be registered to a common center so that the cell features reinforce one another during the reconstruction. U.S. Pat. No. 7,835,561, entitled "Method for Image Processing and Reconstruction of Images for Optical Tomography," discloses error correction techniques for pseudo-projections. U.S. Pat. No. 7,835,561, is hereby incorporated by reference. The set of corrected pseudo-projections is processed using a filtered back-projection algorithm, similar to that in use in conventional X-ray CT, to compute the tomographic 3D cell reconstruction. Pseudo-projection images 110 taken at three angular positions: 0°, 90° and 180° are shown as examples. Illumination is provided by a light source 90 at 585 nm wavelength to optimize image contrast based on the hematoxylin absorption spectrum. In the reconstruction, 3D pixels or voxels are cubic, with a size of 70 nm in each dimension. Data from the plurality of pseudo-projection images is transmitted to a processor 200 which includes a computer program for rendering the pseudo-projection image data into reconstructed 3D cell images. The processor 200 also includes classification training programs and classifier programs as described below.

In one example, stained cells are suspended in a media and injected into a capillary tube having, for example, about a 62 µm inner diameter. In one useful example, a capillary system has been designed to be disposable, thus eliminating the possibility of cross-contamination between specimens. Media and the capillary tube are optically coupled to the condenser and objective lens of the instrument via index-matching fluid placed between the lenses and the capillary. Pressure 114 applied to the fluid moves objects 1 into position for imaging before 3D data is collected as the tube rotates. A mirror 102 is actuated to sweep the plane of focus through the object, and the image is integrated by the camera to create a pseudo-projection from each single perspective. Not shown is the glass holder that interfaces the capillary tube 96 to the optical tomography system. The holder has a hole cut through the middle that is slightly larger than the outside diameter of the capillary and glass flats on either side to allow optical coupling to the objective and condenser lenses. A capillary tube that is loaded with cells embedded in transport medium is threaded through the holder. The transport media that holds the cells, the glass capillary, capillary holder, oil to interface to the lenses and the lenses themselves are made from materials of the same optical index. As a consequence, rays of light pass through the optical tomography system optics, capillary and cells without refraction while the cell is rotated to allow capture of a set of 500 pseudo-projections taken as the capillary rotates through 360 degrees.

Cell Classification

The full potential of the Cell-CT™ technology arises from rapid automated analysis of 3D cell imagery, which can detect cell morphology features that are too subtle or too complex for human reviewers to discern. Furthermore, automated classification eliminates highly variable human review of specimens—a substantial limitation in clinical pathology. Moreover, classification based on 3D images sidesteps inherent limitations associated with classification based on standard 2D, fixed focal plane images, as the 2D slice may not carry the essential image information to comprehensively identify the cell disease state (Raswiki[15]).

To define classifiers to detect abnormal cells a viable system requires three-dimensional, verified, image segmentation to separate the whole cell from the background and the nucleus from the rest of the cell. Also required are a set of morphological features defined to describe various aspects of the cell, cytoplasm, nucleus, and nucleoli. Other useful feature sets are described below and also, for example, in U.S. Pat. No. 9,594,072, issued Mar. 14, 2017, entitled "System and Method for Determining Cell Adequacy in a Cytological Analysis System," to Meyer, et al., for example, the contents of which are incorporated herein by reference.

In one example, 704 features were computed. The features selected represent object shape, volume, distribution of chromatin, and other, more subtle, morphometric elements such as texture. Computation of these features has been verified to be independent of orientation of the cell in a fluid flow, for example. The selected 704 features were computed for each one of the normal and abnormal cells appearing in a sputum specimen. A classifier was trained using methods to address other machine learning problems such as face recognition and voice recognition. These methods include Adaptively Boosted Logistic Regression (Schapire and Freund[18]) and Random Forest (Breiman[3]). Classifier training is described further hereinbelow.

Figure 2:
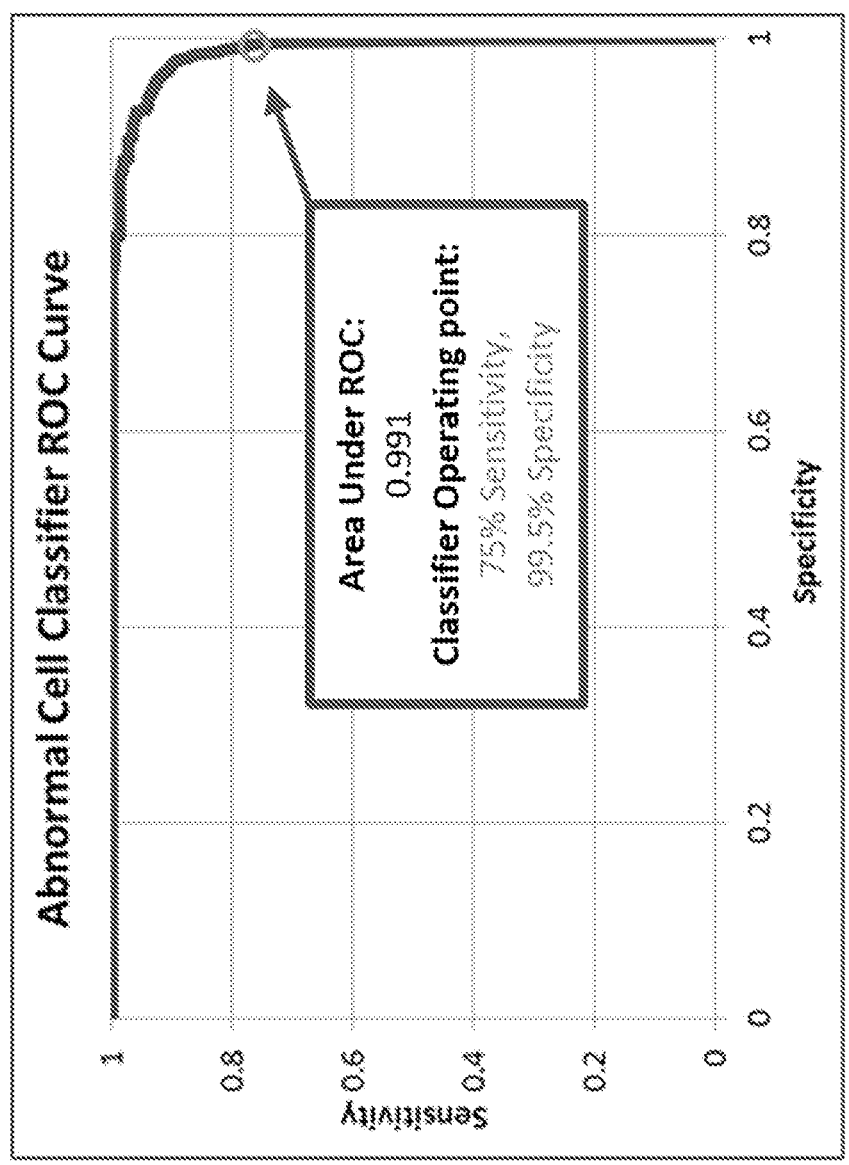
FIG. 2 shows an ROC curve for an abnormal cell classifier.

Referring now to FIG. 2, an ROC curve for an abnormal cell classifier that illustrates the ability of the LuCED® test to isolate and classify abnormal cells that are found in sputum. As evidenced by the classifier operating point at 75% sensitivity and 99.5% specificity there is excellent discrimination between normal and abnormal cells. The published evidence referenced in the background section above shows morphometric changes for malignant cells that correlate to the genomic signature of the cell. This evidence suggests that the genetic mutation responsible for driving the cancer process may be identified through purely morphological methods as provided by an optical tomography system with a 3D reconstruction process such as the Cell CT™ platform and companion LuCED® test.

In one example, determination of the morphological characteristics that correlate to a specific driver mutation can be accomplished by implementing actions including identifying morphometric feature sets that correlate with a driver mutation enabling the identification of cells containing the mutation from other cells in the specimen; isolating malignant cells from other normal cells in the specimen; and separating malignant subtypes. In one more particular example, the act of isolating malignant cells may include isolating adenocarcinoma from other malignant cell types, and isolating a specific driver mutation within the isolated adenocarcinoma.

Figure 3:
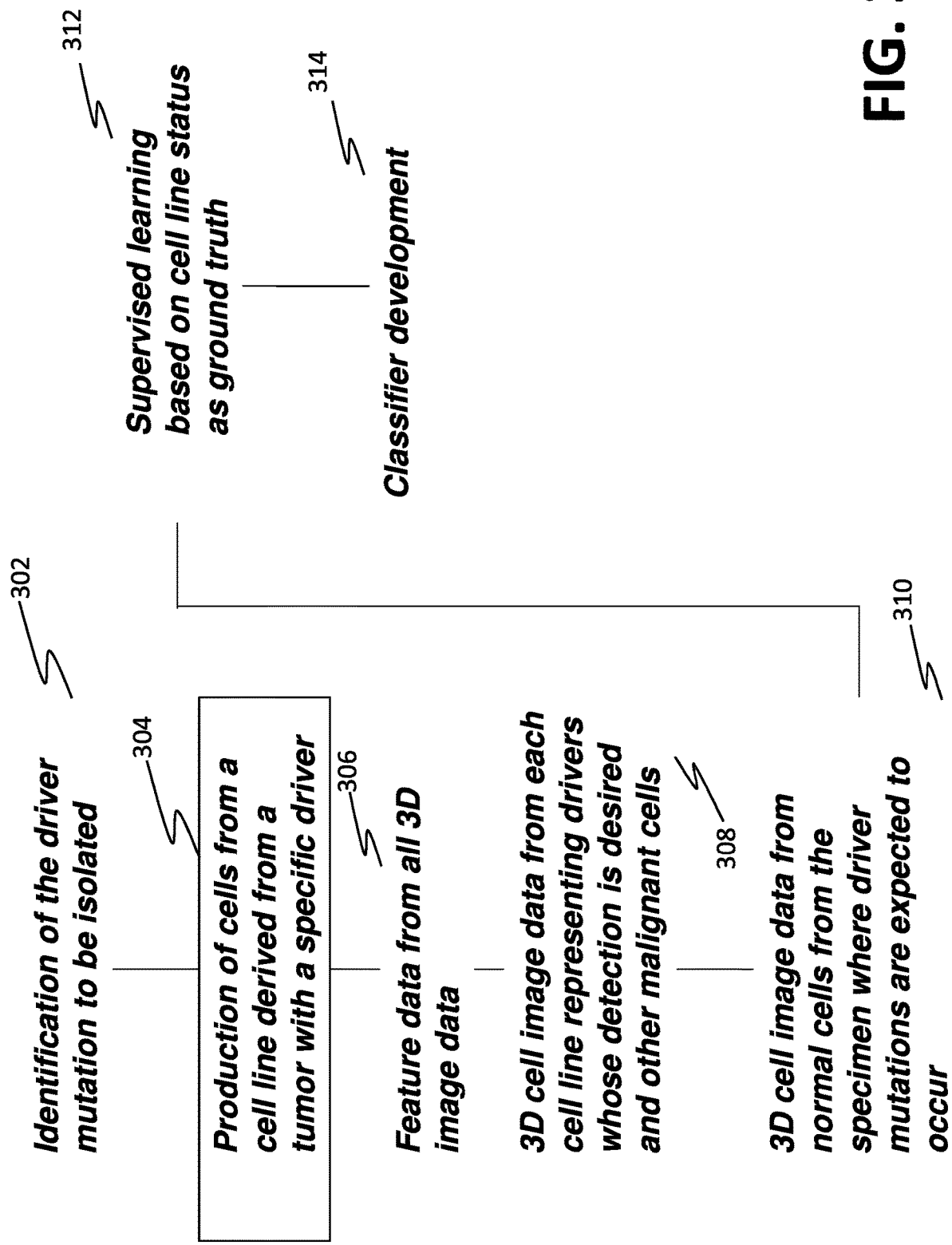
FIG. 3 schematically shows an example of a classification training flow for training classifiers adapted to identify specific mutations associated with different cancer types.

Referring now to FIG. 3, an example of a classification training flow system for training classifiers adapted to identify specific mutations associated with different cancer types is schematically shown. The example described herein was structured to detect driver mutations occurring in lung adenocarcinoma based on a sputum specimen. The method could be generalized for the isolation of any driver mutation associated with any malignant or disease process in cells from a specimen from any organ system.

The classification training flow system, including software processes and hardware apparatus, include identification of the driving mutation to be isolated 302, production of cells from a cell line derived from a tumor with the specific driver 304, identifying 3D image feature data 306, acquiring 3D cell imaging data from each cell line representing drivers whose detection is desired and other malignant cells 308, acquiring 3D cell imaging data from normal cells from the specimen where driver mutations are expected to occur 310, operating supervised learning based on cell line status as ground truth 312, and classifier development 314.

In a first example, identification of the driver mutation to be isolated 302 included identifying adenocarcinoma cells with the below listed cancer drivers:

Adenocarcinoma Cell Lines
A549 (EGFR wild-type, CDKN2A–c.1_471del471, KRAS– p.G12S),
NCI-H1650 (EGFR– p.E746_A750del, CDKN2A– c.1_471del471, TP53– c.673-2A>G),
NCI-H1975 (EGFR-T790M, CDKN2A– p.E69*, PIK3CA– p.G118D, TP53– p.R273H), and
NCI-H2228 (EML4-ALK+, CDKN2A– c.1_471 del471, RB1– p.E204fs*10, TP53– p.Q331* high PD-L1).

In one example, production of cells from a cell line derived from a tumor with a specific driver 304 used the cell lines listed above which were obtained from the American Type Culture Collection (ATCC) and grown according to their recommended specifications. Cells were harvested at ~75% confluence using TrypLE reagent (3 mL per flask). After cells detached they were transferred to a 50 mL tube, and 7 mL medium containing 10% fetal bovine serum was added. After incubation for 20 minutes, the cells were centrifuged for 5 minutes at 200×g, the supernatant aspirated and the cell pellet resuspended in 0.5 mL Phosphate Buffered Saline. 6 mL of Fixcyt (ethanol with added polyethylene glycol) fixative was added to the cells. After 30 minutes, the cells were centrifuged as above and the pellet resuspended in 1 mL of Fixcyt. Cells were either processed immediately for Cell-CT™ platform analysis or stored at −20° C. for later analysis.

In one example, 3D cell image data from normal cells from the specimen where driver mutations are expected to occur 310 normal cells from patients with no known malignancies were processed using the Cell-CT™ platform. Since cancer cells are generally rare in sputum it was desired to create a classifier with high (>99%) specificity. This meant that a large number of normal cells was needed—in the experiment discussed, 15,000 cells were used.

Continuing description of the first example, 3D cell image data from each cell line representing drivers whose detection is desired and other malignant cells 308 cells from each cell line were imaged on the Cell-CT™ platform. A target 75% sensitivity was desired. This implied collection of at least 500 cells from each cell line to ensure variance about the 75% target did not exceed 5%.

Feature data from all 3D image data 306 included reconstructed 3D cell images that were processed to yield 704 structural biomarkers as features to define various elements of cell morphology. Examples of features included, but were not limited to:

Cell volume;
Nuclear volume;
Ratio of nuclear to cytoplasm volume;
Shape features to define pleomorphisms in the nuclear envelope;
Features to characterize distribution and texture of the chromatin within the nucleus;
Features to count and find the size of nucleoli; and
Features to represent the appearance of nuclear grooves.

In general, features have measured values and may be compared to a set of threshold values determined during classifier training in order to identify a particular cell type based on a plurality of features. For example, normal cells will exhibit features within a normal range of feature values. Since cells from normal patients and cell lines were used, supervised learning based on cell line status as ground truth 312 proceeded on the assumption of a homogeneous cell population within each group of cells. This implies that there is no need for independent confirmation of the cells used in the study. In other cases, ground truth could be established through pathology studies and the like, for example, to confirm the status of cells to be used as ground truth.

Figure 4:
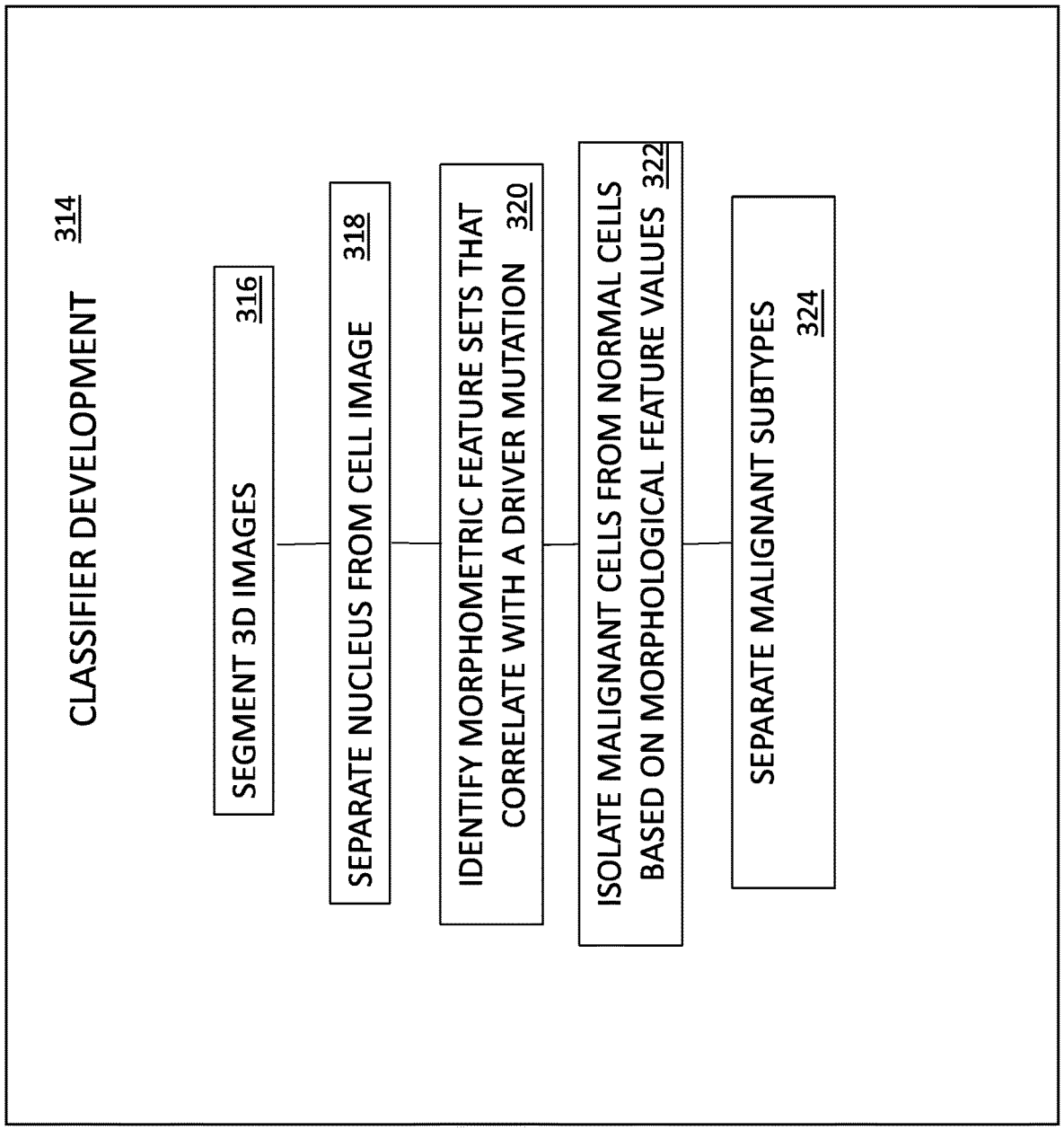
FIG. 4 schematically shows a more detailed process of an example of classifier development for defining a classifier to detect abnormal cells using morphological features that correlate with driver mutations.

Referring now to FIG. 4, a more detailed process of an example of classifier development for defining a classifier to detect abnormal cells using morphological features that correlate with driver mutations is schematically shown and described. Classifier development 314 is a process typically implemented on a computer processor using computer software algorithms including software algorithms to segment 3D images 316, separate a nucleus from each cell image 318, identifying morphometric feature sets that correlate with a driver mutation 320, isolate malignant cells from normal cells based on morphological feature values 322 and separate malignant subtypes 324.

Figure 5:
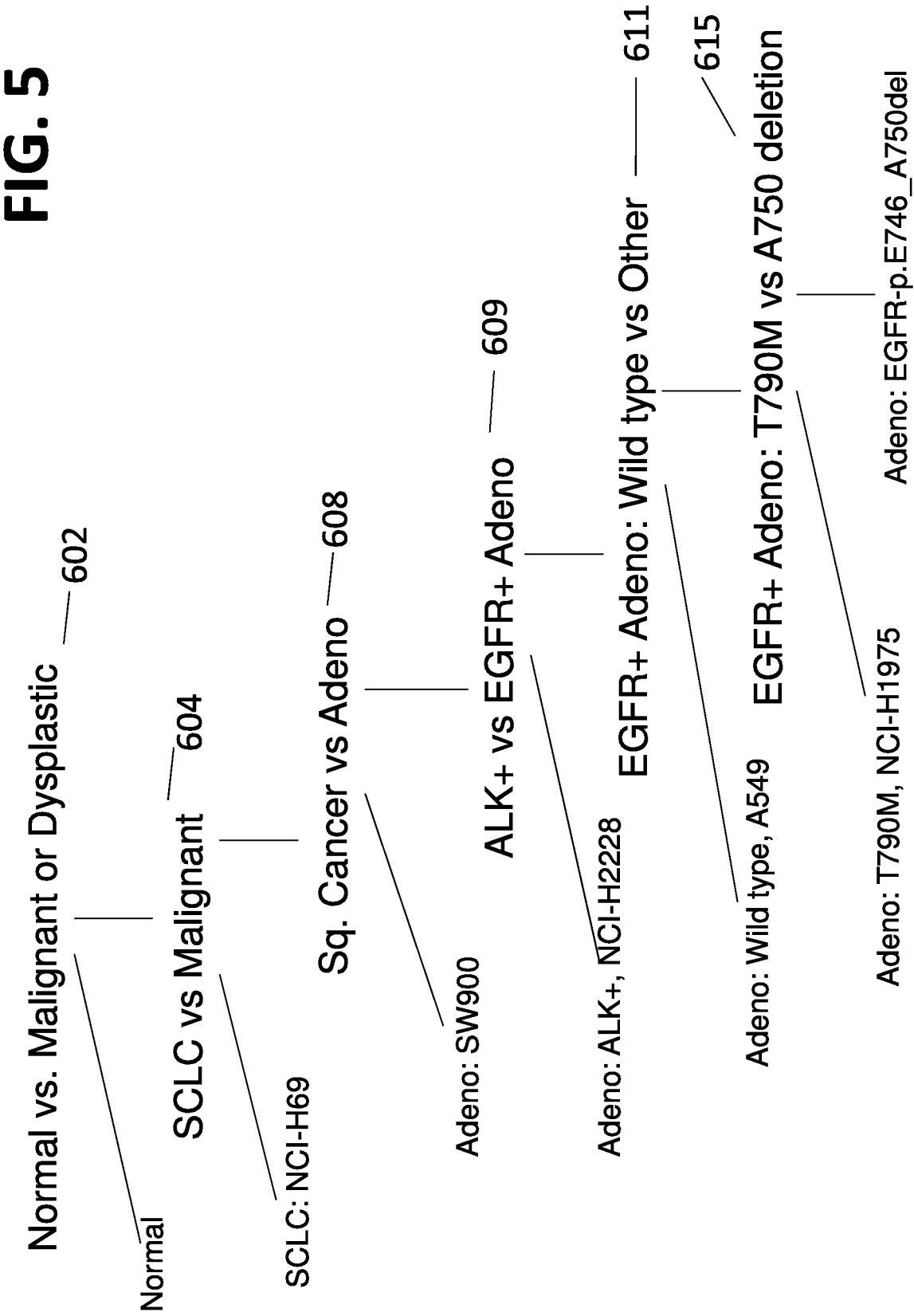
FIG. 5 schematically shows an example of classification cascade to identify specific mutations associated with different cancer types.

Referring now to FIG. 5, an example of a classification cascade for training classifiers adapted to identify specific mutations associated with different cancer types is shown. Training proceeded to produce a series of binary classifiers to isolate the desired cells including a first classifier 602, a second classifier 604, a third classifier 608, a fourth classifier 609, a fifth classifier 611, and a sixth classifier 615.

In one example, the first classifier 602 was trained for isolation of malignant cells from other normal cells. The first classifier 602 groups all the data from the malignant cell lines and assigns it to one class, for example, a set of malignant cells. The set of malignant cells plus the normal cells as negative control were used to train the first classifier to separate normal from malignant cells. This step is especially critical as malignant cells are rare in sputum. A manual review is conducted on only a very small portion of the cells in sputum. Since the manual review is a part of the process, it may be assumed that only abnormal cells that emerge from the process are truly malignant and may then be subtyped using the classifiers described below.

The second classifier 604 separates malignant subtypes. Any organ system has different types of tissue associated with it. For example, lung tissue is comprised of squamous epithelium and adenomatous tissue from the bronchi. Small cell lung cancer (SCLC) cells from the neuroendocrine glands are also sometime in evidence. Thus, a classifier is needed to isolate the specific cancer subtype in which the desired driver mutation occurs. This is done by first isolating small cell lung cancer from adenocarcinoma and squamous cancer and then isolating adenocarcinoma from squamous cancer. Further isolation of the desired mutation subtype within adenocarcinoma proceeds stepwise. The grouping of cell lines selected as a training set for this example is given in Table 1 below. Isolation of specific driver mutations is determined based on morphological factors in the third through sixth classifiers 608, 609, 611 and 615.

TABLE 1

| Classifier | Target Cell Type - Class1 | Cell Population - Class0 |
|---|---|---|
| Normal vs. Malignant or Dysplastic | Normal | NCI-H69, SW-900, A549, NCI-H1650, NCI-H1975, NCI-H2228 |
| SCLC vs Malignant | NCI-H69 | SW-900, A549, NCI-H1650, NCI-H1975, NCI-H2228 |
| Sq. Cancer vs Adeno | SW900 | A549, NCI-H1650, NCI-H1975, NCI-H2228 |
| ALK+ vs EGFR+ Adeno | NCI-H2228 | A549, NCI-H1650, NCI-H1975 |
| EGFR+ Adeno: Wild type vs Other | A549 | NCI-H1650, NCI-H1975 |
| EGFR+ Adeno: T790M vs A750 deletion | NCI-H1975 | NCI-H1650 |

Still referring to FIG. 5, in one example, the stepwise isolation of mutation drivers begins with the first classifier 602 where a set of cells is isolated into normal and malignant or dysplastic classes. Any cells identified as malignant are further processed in the second classifier 604 which isolates SCLC: NCI-H69 type cells from other malignant cells which are passed to the third classifier 608. The third classifier 608 isolates Adeno: SW900 from other adenocarcinoma type cells and passes the other cells of the fourth classifier 609. The fourth classifier 609 isolates Adeno: ALK+, NCI-H2228 cell types from other remaining cell types and passes the remaining cell types to the fifth classifier 611. The fifth classifier 611 isolates Adeno: Wild type, A549 from EGFR+ Adeno cell types and passes the EGFR+ Adeno subtypes to the fifth classifier 615. The sixth classifier 615 isolates Adeno: T790M, NCI-H1975 from Adeno: EGFR-p.E746_A750del.

Those skilled in the art will recognize that this is only one example of an application of the invention and that other cell types and mutation drivers can be used to build and train classifiers according to the methods described herein. The invention is not limited in any way to this example. Classifier decisions are implemented by establishing decision boundary values for any measurable characteristic of a feature during classifier training. Thresholds may be selected or set according to instrument specifications, acceptable error rates, statistics, or other criteria according to accepted pattern recognition principles.

Experimental Results

Figure 6:
FIG. 6 tabulates results of an experimental study in a table that indicates the area under the ROC (aROC) and sensitivity and specificity for a target cell.

Referring now to FIG. 6 where results of one experimental study are summarized in a table. A table 650 indicates the area under the ROC (aROC) 652 and the sensitivity 654 and specificity 656 for a target cell as classified by classifiers trained according to the training methods described above. Specificities relate to mis-identification of the malignant cells by a classifier that was intended to isolate a specific driver mutation. For example, the specificity for identification of cells from a small cell lung cancer (SCLC) tumor is 99.98%. The small number of cells that are called SCLC are in-fact from some of the other cell lines the table 650. Since only 0.02% of the malignant cells are misidentified the positive predictive value can be computed for identification of SCLC as PPV=TP/(TP+FP)=100*0.748/(0.748+0.002)=99.7.

Figure 7:
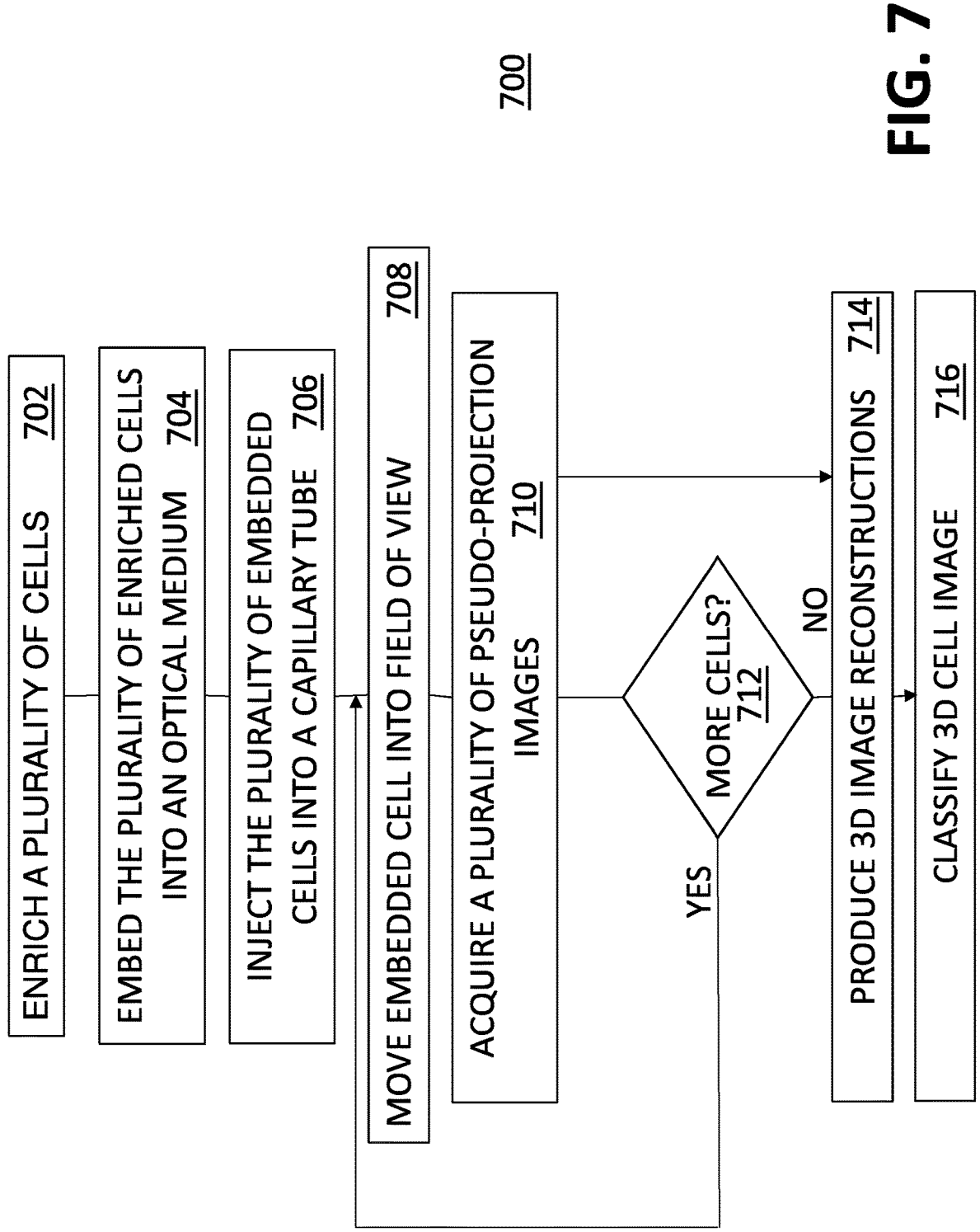
FIG. 7 schematically shows a block diagram of a method and system for genotyping of cells in fluid flow in a capillary tube using optical tomography.

Referring now to FIG. 7, a block diagram of a method and system for genotyping of cells in fluid flow in a capillary tube using optical tomography is schematically shown. A system 700 implements a method including functional acts of enriching a plurality of cells 702, embedding the plurality of enriched cells into an optical medium 704, injecting the plurality of embedded cells into a capillary tube 706, moving each embedded cell into a field of view 708, requiring a plurality of pseudo-projection images of the cell 710. Once the pseudo-projection images are obtained, a decision point 712 queries whether there are more cells in the capillary tube to be moved into the field of view. If there are more cells to be imaged, the system returns to functional act 708 and repeats until all cells have been imaged. As cells are imaged, images are sent to be processed at functional act 714 for producing 3D image reconstructions from the pseudo-projection images. The 3D images are then further processed by classifiers as described above to determine the cell types from morphological features derived from mutation drivers. The classifiers compare feature values to training-derived thresholds for a plurality of image features in order to classify a cell into a cell type.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment and devices, and that various modifications, both as to the equipment details and operating procedures, may be accomplished without departing from the true spirit and scope of the present invention.

REFERENCES

The teachings of the following publications are incorporated herein in their entirety by this reference.
1) Bougen-Zhukov et al., 2017. Large-scale image-based screening and profiling of cellular phenotypes. Cytometry A. 91(2):115-125.
2) Bray et al., 2012. Workflow and metrics for image quality control in large-scale high-content screens. J Biomol Screen. 17(2):266-74.
3) Breiman L. 2001. Random Forests. Machine Learning. 45(1):5-32.
4) Deans, S. 2007. The Radon Transform and some of its applications. Malabar: Dover.
5) Fauver M, Seibel E, Rahn J R, Meyer M, Patten F, Neumann T, Nelson A. 2005. Three-dimensional imaging of single isolated cell nuclei using optical projection tomography. Optics Express.; 13(11):4210-4223. [PubMed: 19495335]
6) Finkelstein et al., 2012. Papillary thyroid carcinomas with and without BRAF V600E mutations are morphologically distinct. Histopathology. 60:1052-9.
7) Fuchs et al., 2010. Clustering phenotype populations by genome-wide RNAi and multiparametric imaging. Mol Syst Biol. 6:370.
8) Hansen and Siu, 2016. PD-L1 Testing in Cancer: Challenges in Companion Diagnostic Development. JAMA Oncol. 2(1):15-16.
9) Meyer et al., 2015. The Cell-CT 3-dimensional cell imaging technology platform enables the detection of lung cancer using the noninvasive LuCED sputum test. Cancer Cytopathol. 123(9):512-23.
10) Mukherji et al., 2006. Genome-wide functional analysis of human cell-cycle regulators.

11) Proc Natl Acad Sci USA. 103(40):14819-24.
12) Nishino et al., 2012. Histologic and cytomorphologic features of ALK-rearranged lung adenocarcinomas. Mod Pathol. 25(11):1462-72.
13) Nicolazzo et al., 2016. Monitoring PD-L1 positive circulating tumor cells in non-small cell lung cancer patients treated with the PD-1 inhibitor Nivolumab. Sci Rep. 2016; 6:31726.
14) Patel S P, Kurzrock R. 2015. PD-L1 Expression as a Predictive Biomarker in Cancer Immunotherapy. Mol Cancer Ther.14:847-56.
15) Raswiki. [Accessed Mar. 19, 2015] Maximum intensity projection (MIP). Retrieved from Radiopaedia.org
16) Rohban et al., 2017. Systematic morphological profiling of human gene and allele function via Cell Painting. Elife. 6. pii: e24060.
17) Rossi et al., 2014. Morphological parameters able to predict BRAF(V600E) -mutated malignancies on thyroid fine-needle aspiration cytology: Our institutional experience. Cancer Cytopathol. 122:883-91.
18) Schapire, R.; Freund, Y. Boosting, foundations and algorithms. Cambridge: MIT press; 2012.
19) Singh et al., 2009. A gene expression signature associated with "K-Ras addiction" reveals regulators of EMT and tumor cell survival. Cancer Cell 15(6):489-500.
20) Suda et al., 2009. EGFR T790M mutation: a double role in lung cancer cell survival? J Thorac Oncol. 4(1):1-4.
21) Vécsey-Semjén et al., 2002. Novel colon cancer cell lines leading to better understanding of the diversity of respective primary cancers. Oncogene 21(30):4646-62.
22) Wilbur et al., 2015. Automated 3-dimensional morphologic analysis of sputum specimens for lung cancer detection: Performance characteristics support use in lung cancer screening. Cancer Cytopathol. 123(9):548-56.
23) Xu et al., 2015. Up-regulation of the Hippo pathway effector TAZ renders lung adenocarcinoma cells harboring EGFR-T790M mutation resistant to gefitinib. Cell BioScan. 5:7

What is claimed is:

1. A classification training method for training classifiers adapted to identify specific mutations associated with cancer comprises:
   identifying a plurality of cancer driver mutations;
   acquiring a plurality of first cells from a plurality of mutation cell lines derived from conditions having the plurality of cancer driver mutations;
   identifying 3D image feature data from the plurality of first cells;
   generating a first set of 3D cell imaging data from the plurality of first cells and from a plurality of other malignant cells, where the first set of cell imaging data includes a plurality of first individual cell images;
   generating a second set of 3D cell imaging data from a set of normal cells where the plurality of driver mutations is expected to occur, where the second set of cell imaging data includes a plurality of second individual cell images;
   operating supervised learning based on cell line status as ground truth; and generating a classifier from the supervised learning.

2. The method of claim 1 wherein the act of identifying 3D image feature data comprises processing reconstructed 3D cell images to define a plurality of features of cell morphology.

3. The method of claim 2 wherein the plurality of features is selected from the group consisting of cell volume, nuclear volume, ratio of nuclear to cytoplasm volume, shape features to define pleomorphisms in the nuclear envelope, features to characterize distribution and texture of the chromatin within the nucleus, features to count and find the size of nucleoli, features to represent the appearance of nuclear grooves and combinations thereof.

4. The method of claim 1 wherein generating a classifier comprises: segmenting each of the plurality of first individual cell images; separating a nucleus from the segmented first cell image;
   identifying a plurality of morphometric feature sets that correlate with each driver mutation from the plurality of driver mutations;
   isolating malignant cells from normal cells by comparing morphological feature values; and
   separating malignant subtypes.

5. The method of claim 1 where generating a classifier further comprises producing a series of binary classifiers to isolate a plurality of target cells derived from the plurality of first cells.

6. The method of claim 5 wherein producing a series of binary classifiers comprises: producing a first classifier trained for isolation of malignant cells from other normal cells;
   producing a second classifier for separating malignant subtypes; and producing at least one subsequent classifier to isolate mutation driver cell subtypes.

7. The method of claim 6 wherein the act of isolating malignant cells comprises isolating adenocarcinoma from other malignant cell types; and isolating a specific driver mutation within adenocarcinoma.

8. The method of claim 7 wherein the adenocarcinoma is selected from the group consisting of Adenocarcinoma cell lines, A549 (EGFR wild-type, CDKN2A–c.1_471del471, KRAS– p.G12S), NCI-H1650 (EGFR– p.E746_A750del, CDKN2A– c.1_471del471,TP53– c.673-2A>G), NCI-H1975 (EGFR-T790M, CDKN2A– p.E69*, PIK3CA– p.G118D, TP53– p.R273H), NCI-H2228 (EML4-ALK+, CDKN2A– c.1_471del471, RB1– p.E204fs*10, TP53– p.Q331* high PD-L1) and combinations thereof.

9. The method of claim 1 wherein the plurality of cells is selected from the group consisting of a biological cell, bronchial epithelial cells, a cell nucleus, an organelle, a human cell, mammal cell, a microscopic biological feature and combinations thereof.

10. The method of claim 1 wherein the plurality of cells is selected from the group consisting of objects obtained from specimens including sputum, blood, urine, cervical scrapes, bowel scrapes, skin scrapes, plural effusion and a liquid biopsy.

11. A classifier trained in accordance with the method of claim 1.

12. A method for morphometric genotyping of cells in fluid flow in a capillary tube using optical tomography comprising:
   a) enriching a plurality of cells;
   b) embedding the plurality of enriched cells into an optical medium;
   c) injecting the plurality of embedded cells into a capillary tube;
   d) applying pressure to the plurality of embedded cells until at least one of the plurality of embedded cells appears in a field of view of an optical tomography viewing subsystem;

e) operating the optical tomography system to acquire a plurality of pseudo-projection images of the at least one embedded cell that is in the field of view by rotating the capillary tube about a tube axis to generate a plurality of pseudo-projection images at different views;

f) repeating acts d) and e) to provide a set of pseudo-projection images for each embedded cell;

g) reconstructing each embedded cell using data from the set of pseudo-projection images to produce a set of multiple cell image reconstructions;

h) segmenting each multiple image of the set of multiple cell image reconstructions to separate a cell image from background;

i) further segmenting the cell image to separate a nucleus from the cell image;

j) computing a plurality of morphological features characteristic of mutation drivers from each cell image;

k) operating a biological specimen classifier to determine a feature value from the plurality of morphological features characteristic of mutation drivers, wherein the biological specimen classifier is trained in accordance with the method of claim 1; and l) classifying the multiple cell image into a cell type category by comparing the feature value to a predetermined threshold value.

13. A method for stepwise isolation of a plurality of cancer mutation drivers comprises:

providing a plurality of 3D reconstruction images to a first morphological classifier, where the 3D reconstruction images represent a plurality of cell types;

operating the first morphological classifier to isolate the plurality of cell types into normal and malignant cell types or dysplastic cell types;

next, operating a second morphological classifier on the malignant cell types to isolate SCLC: NCI-H69 type cells from other malignant cells;

next, operating a third morphological classifier on the other malignant cells to isolate Adena: SW900 from other adenocarcinoma type cells;

next, operating a fourth morphological classifier on the other adenocarcinoma type cells to isolate Adena: ALK+, NCI-H2228 cell types from other remaining cell types;

next, operating a fifth morphological classifier on the other remaining cell types to further isolate Adena: Wild type, A549 from EGFR+ Adena cell types; and next, operating a sixth morphological classifier to further isolate Adena: T790M, NCI-H1975 from Adena: EGFR-p.E746_A750del.

14. The method of claim 13 wherein the 3D reconstructions images are derived from a plurality of optical tomography cell images.

15. The method of claim 13 wherein the first through sixth classifiers are generated by acts comprising:

segmenting each of the plurality of 3D reconstruction images; separating a nucleus from each segmented cell image;

identifying a plurality of morphometric feature sets that correlate with each cancer driver mutation from the plurality of cancer driver mutations;

isolating malignant cells from normal cells by comparing morphological feature values; and separating malignant subtypes.

16. The method of claim 15 where generating a classifier further comprises producing a series of binary classifiers to isolate a plurality of target cells derived from the plurality of first cells.

17. The method of claim 16 wherein producing a series of binary classifiers comprises:

producing a first classifier trained for isolation of malignant cells from other normal cells;

producing a second classifier for separating malignant subtypes; and producing at least one subsequent classifier to isolate mutation driver cell subtypes.

18. The method of claim 17 wherein the act of isolating malignant cells comprises isolating adenocarcinoma from other malignant cell types; and isolating a specific driver mutation within adenocarcinoma.

19. A classification training system for training classifiers adapted to identify specific mutations associated with cancer comprises:

means for identifying a plurality of driver mutations;

means for acquiring a plurality of first cells from a plurality of mutation cell lines derived from conditions having the plurality of driver mutations;

means for identifying 3D image feature data from the plurality of first cells;

means for generating a first set of 3D cell imaging data from the plurality of first cells and from a plurality of other malignant cells, where the first set of cell imaging data includes a plurality of first individual cell images;

means for generating a second set of 3D cell imaging data from a set of normal cells where the plurality of driver mutations is expected to occur, where the second set of cell imaging data includes a plurality of second individual cell images;

means for operating supervised learning based on cell line status as ground truth; and means for generating a classifier from the supervised learning.

20. The system of claim 19 wherein the means for of identifying 3D image feature data comprises processing reconstructed 3D cell images to define a plurality of features of cell morphology.

21. The system of claim 20 wherein the plurality of features is selected from the group consisting of cell volume, nuclear volume, ratio of nuclear to cytoplasm volume, shape features to define pleomorphisms in the nuclear envelope, features to characterize distribution and texture of the chromatin within the nucleus, features to count and find the size of nucleoli, features to represent the appearance of nuclear grooves and combinations thereof.

22. The system of claim 19 wherein the means for generating a classifier comprises: a processor including a program for segmenting each of the plurality of first individual cell images;

the processor further including a program for separating a nucleus from the segmented first cell image;

the processor further including a program for identifying a plurality of morphometric feature sets that correlate with each driver mutation from the plurality of driver mutations;

the processor further including a program for isolating malignant cells from normal cells by comparing morphological feature values; and the processor further including a program for separating malignant subtypes.

23. The system of claim 22 where the means for generating a classifier further comprises the processor further including a program for producing a series of binary classifiers to isolate a plurality of target cells derived from the plurality of first cells.

24. The system of claim 23 wherein the means for producing a series of binary classifiers comprises:
   the processor further including a program for producing a first classifier trained for isolation of malignant cells from other normal cells;
   the processor further including a program for producing a second classifier for separating malignant subtypes; and
   the processor further including a program for producing at least one subsequent classifier to isolate mutation driver cell subtypes.

25. The system of claim 24 wherein the program for producing a first classifier trained for isolation of malignant cells from other normal cells comprises
   a program for isolating adenocarcinoma from other malignant cell types; and a program for isolating a specific driver mutation within adenocarcinoma.

26. The system of claim 25 wherein the adenocarcinoma is selected from the group consisting of Adenocarcinoma cell lines, A549 (EGFR wild-type, CDKN2A- c.1_471del471, KRAS- p.G12S), NCI-H1650 (EGFR- p.E746_A750del, CDKN2A- c.1_471del471,TP53- c.673-2A>G), NCI-H1975 (EGFR-T790M, CDKN2A- p.E69*, PIK3CA- p.G118D, TP53- p.R273H), NCI-H2228 (EML4-ALK+, CDKN2A- c.1_471del471, RB1- p.E204fs*10, TP53- p.Q331* high PD-L1) and combinations thereof.

27. The system of claim 19 wherein the plurality of cells is selected from the group consisting of a biological cell, bronchial epithelial cells, a cell nucleus, an organelle, a human cell, mammal cell, a microscopic biological feature and combinations thereof.

28. The system of claim 19 wherein the plurality of cells is selected from the group consisting of objects obtained from specimens including sputum, blood, urine, cervical scrapes, bowel scrapes, skin scrapes, plural effusion and a liquid biopsy.

* * * * *